United States Patent [19]
Byk et al.

[11] Patent Number: 6,107,286
[45] Date of Patent: Aug. 22, 2000

[54] LIPOPOLYAMINES AS TRANSFECTION AGENTS AND PHARAMACEUTICAL USES THEREOF

[75] Inventors: Gérardo Byk, Creteil; Daniel Scherman, Paris; Catherine Dubertret, Sevres, all of France

[73] Assignee: Rhône-Poulenc Rorer S.A., Antony, France

[21] Appl. No.: 08/849,497

[22] PCT Filed: Dec. 4, 1995

[86] PCT No.: PCT/FR95/01595

§ 371 Date: Jun. 4, 1997

§ 102(e) Date: Jun. 4, 1997

[87] PCT Pub. No.: WO96/17823

PCT Pub. Date: Jun. 13, 1996

[30] Foreign Application Priority Data

Dec. 5, 1994 [FR] France ................................... 94/14596

[51] Int. Cl.[7] ........................................................ A61K 31/70
[52] U.S. Cl. ......................... 514/44; 560/170; 560/180; 560/157; 560/158; 560/188; 564/224
[58] Field of Search ................................... 560/170, 180, 560/157, 158, 188; 564/224; 514/44

[56] References Cited

U.S. PATENT DOCUMENTS

| | | |
|---|---|---|
| 4,014,933 | 3/1977 | Boettger et al. . |
| 5,616,745 | 4/1997 | Behr . |
| 5,641,662 | 6/1997 | Debs et al. . |

FOREIGN PATENT DOCUMENTS

| | | |
|---|---|---|
| 394111 | 10/1990 | European Pat. Off. . |
| 2066157 | 8/1971 | France . |
| WO 9405624 | 3/1994 | WIPO . |
| WO 96/22765 | 8/1996 | WIPO . |

OTHER PUBLICATIONS

Chem Abstract, 1991:217, Shvelashvili et al, rn=107–15–3 Month Unavailable 1990.

Behr, J.–P. et al., Efficient Gene Transfer into Mammalian Primary Endocrine Cells with Lipopolyamine–coated DNA, Proceedings of the National Academy of Sciences of USA, 86, 6982–6986 (1989) Month Unavailable.

Remy, J–S. et al., Gene Transfer with a Series of Lipophilic DNA–Binding Molecules, Bioconjugate Chemistry, 5, 647–654 (1994) Month Unavailable.

Behr, J–P., DNA Strongly Binds to Micelles and Vesicles Containing Lipopolyamines or Lipointercalants, Tetrahedron Letters, 27, 5861–5864 (1986) Month Unavailable.

*Primary Examiner*—Samuel Barts
*Attorney, Agent, or Firm*—Synnestvedt & Lechner LLP

[57] ABSTRACT

Cationic lipids of general formula (I), wherein m is an integer from 2 to 6 inclusive; n is an integer from 1 to 9 inclusive, preferably 1–5, where, when n is 2–9, a single R grouping other than hydrogen is present in the general formula, and m has variable or identical values within the groupings (a) or —$(CH_2)_m$; R is a hydrogen atom or a radical of general formula (II), wherein X or $X^1$, which are the same or different, are an oxygen atom, a methylene grouping —$(CH_2)_q$— where q is 0, 1, 2 or 3, or an amino grouping —NH— or $NR^1$—, where R is a $C_{1-4}$ alkyl grouping; Y and $Y^1$, which are the same or different, are a hydrogen atom or an optionally substituted $C_{1-4}$ alkyl radical, and p is 0–5; and $R_6$ is a cholesterol derivative or an alkylamino grouping —$NR_1R_2$, where $R_1$ and $R_2$ are, independently of each other, a straight or branched, saturated or unsaturated $C_{12-22}$ aliphatic radical. Pharmaceutical compositions containing said lipids, and their uses for transfecting nucleic acids whether in vitro or in vivo in cells, are also disclosed.

25 Claims, No Drawings

LIPOPOLYAMINES AS TRANSFECTION AGENTS AND PHARAMACEUTICAL USES THEREOF

The present invention relates to novel compounds belonging to the family of lipopolyamines, to pharmaceutical compositions containing them and to their applications for the in vivo and/or in vitro transfection of nucleic acids.

Many genetic diseases are associated with an expression defect and/or abnormal expression, that is to say deficient or excessive expression, of one or more nucleic acids. The main aim of gene therapy is to correct genetic anomalies of this type by means of in vivo or in vitro cellular expression of cloned genes.

At the present time, several methods are proposed for the intracellular delivery of genetic information of this type. One of these methods, in particular, is based on the use of chemical or biochemical vectors. Synthetic vectors have two main functions, to compact the DNA to be transfected and to promote its binding to the cell as well as its passage across the plasma membrane and, where appropriate, across the two nuclear membranes.

Significant progress was made in this mode of transfection with the development of technology based on the use of a cationic lipid. It has thus been demonstrated that a positively charged cationic lipid, N-[1-(2,3-dioleyloxy)propyl]-N,N,N-trimethylammonium (DOTMA) chloride, interfered, in the form of liposomes or small vesicles, spontaneously with DNA, which is negatively charged, to form lipid-DNA complexes capable of fusing with cell membranes, and thus allowed the intracellular delivery of the DNA. However, although this molecule is effective as regards transfection, it has the disadvantage of being non-biodegradable and of having a toxic nature towards cells.

Since DOTMA, other cationic lipids have been developed on this structural model: lipophilic groups associated with an amino group via a so-called "spacer" arm. Among these lipids, there may more particularly be mentioned those comprising, as lipophilic group, two fatty acids or a cholesterol derivative, and also containing, where appropriate, as free amino group, a quaternary ammonium group. DOTAP, DOBT or ChOTB may be mentioned in particular as representatives of this category of cationic lipids. Other compounds, such as DOSC and ChOSC, are characterized by the presence of a choline group in place of the quaternary ammonium group. In general, however, the transfecting activity of these compounds remains fairly low.

Another category of cationic lipids, the lipopolyamines, has also been described. In this type of compound, the cationic group is represented by the L-5-carboxyspermine radical which contains four ammonium groups, two primary and two secondary. DOGS and DPPES in particular form part thereof. These lipopolyamines are more particularly effective for the transfection of primary endocrine cells.

In fact, an ideal synthetic transfection agent should exhibit a high level of transfection for a wide spectrum of cells, should have no toxicity or, at least, a very minimized toxicity at the doses of use, and, lastly, should be biodegradable so as to rid itself of any side effects on the treated cells.

The very subject of the present invention is indeed to propose novel compounds which are capable of being used effectively in the in vitro and/or in vivo transfection of cells and, in particular, for the vectorization of nucleic acids.

The first subject of the invention is lipopolyamines, in D, L or DL form and the salts thereof, represented by the general formula I:

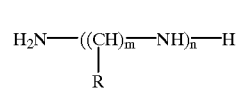

in which
m is an integer between 2 and 6 inclusively,
n is an integer between 1 and 9 inclusively and more preferably between 1 and 5 with a single group R other than hydrogen present in the general formula and values of m which are variable or identical in the various groups

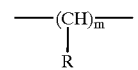

and —$(CH_2)_m$—
R represents a hydrogen atom or a radical of general formula II

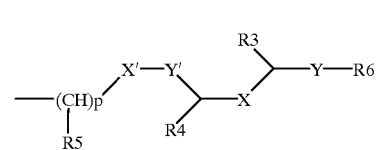

in which
X and X' represent, independently of each other, an oxygen atom, a methylene group —$(CH_2)_q$— with q equal to 0, 1, 2 or 3, or an amino group —NH— or —NR'— with R' representing a $C_1$ to $C_4$ alkyl group,
Y and Y' represent, independently of each other, a methylene group, a carbonyl group or a C=S group,
$R_3$, $R_4$ and $R_5$ represent, independently of each other, a hydrogen atom or a substituted or unsubstituted $C_1$–$C_4$ alkyl radical, with it being possible for p to range between 0 and 5,
$R_6$ represents a cholesterol derivative or an alkylamino group —$NR_1R_2$ with $R_1$ and $R_2$ representing, independently of each other, a linear or branched, saturated or unsaturated $C_{12}$ to $C_{22}$ aliphatic radical.

Of most particular interest are the compounds in which R is represented therein by the general formula II'

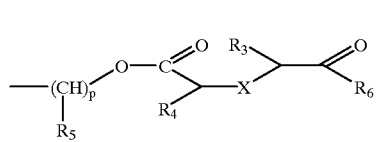

in which $R_3$, $R_4$, $R_5$, $R_6$ and p correspond to the above definitions and X represents an oxygen atom or a group —$(CH_2)_q$— with q being equal to zero.

This family of compounds is characterized in particular by the presence of an internal ester bond, which is advantageous in terms of the biodegradability.

As preferred lipopolyamines according to the invention, there may more particularly be mentioned the following compounds:

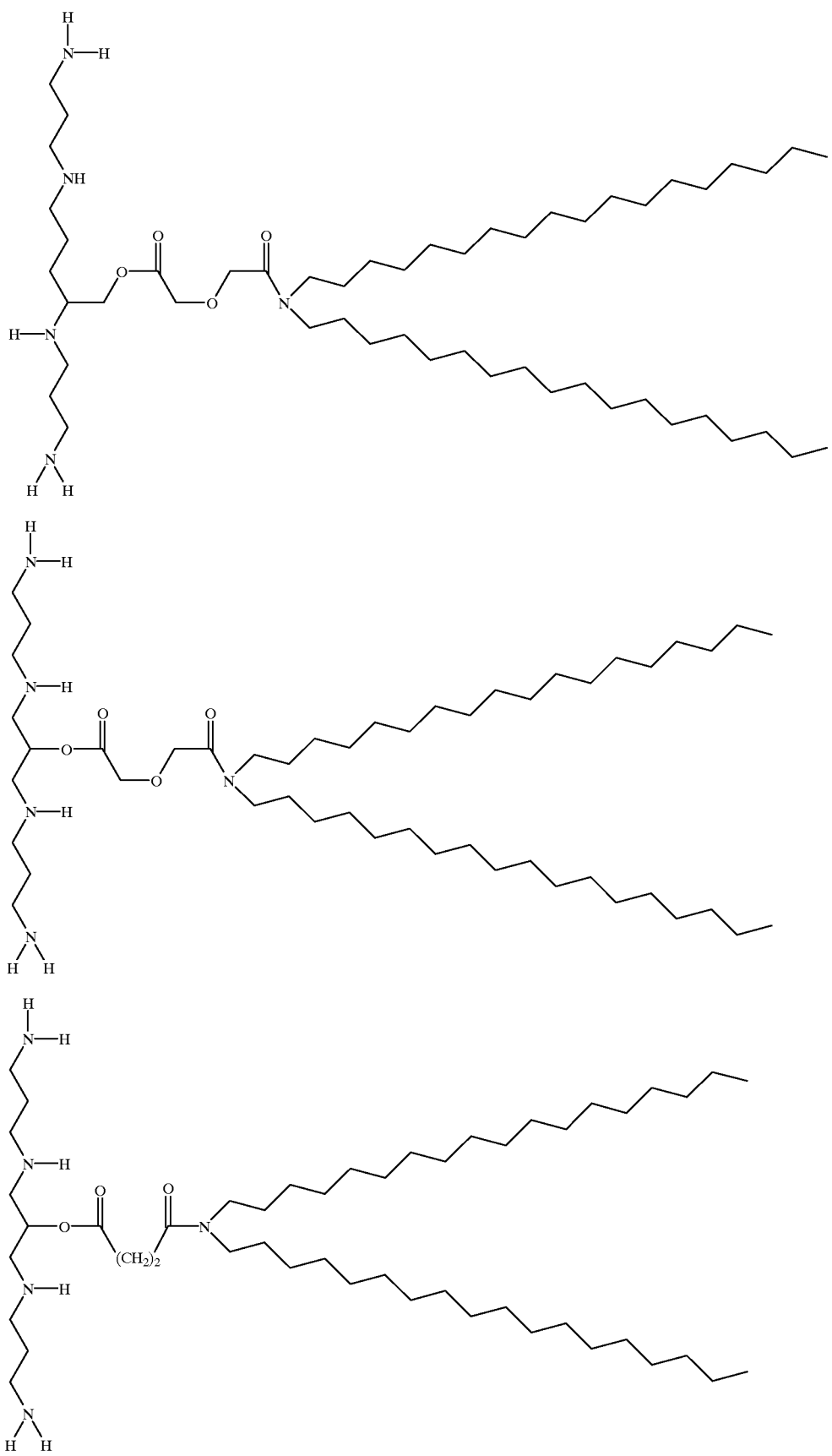

-continued

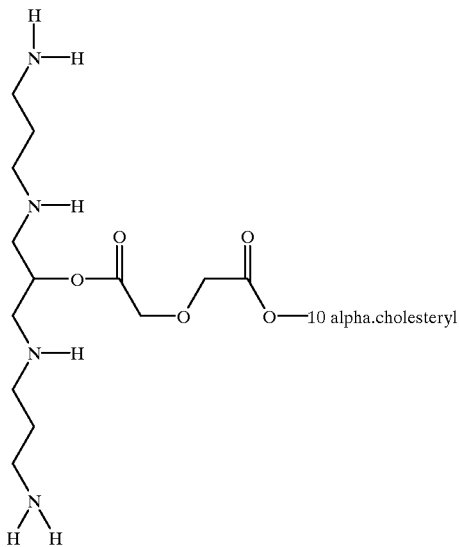

in the D, L or DL form or one of the salts thereof.

Another subject of the present invention is any therapeutic application of the lipopolyamines according to the invention, either directly or in pharmaceutical compositions.

As discussed above, the compounds of general formula I prove to be most particularly advantageous for the in vitro and in vivo transfection of nucleic acids. They compact DNA effectively and advantageously exhibit very much reduced toxicity or even no toxicity towards treated cells. In addition, they are biodegradable in particular by hydrolysis of their ester bond.

In order to obtain a maximum effect for the compositions of the invention, the respective proportions of the compound of general formula I and of the nucleic acid are preferably determined such that the ratio R—positive charges of the lipopolyamine considered to negative charges of the said nucleic acid—is optimal. As this optimum ratio varies in particular according to the mode of use, namely in vivo or in vitro, and according to the type of cell to be transfected, it is optimized from case to case. This optimization falls within the competence of those skilled in the art.

In the compositions of the present invention, the polynucleotide may either be a deoxyribonucleic acid or a ribonucleic acid. It may be sequences of natural or artificial origin, and in particular genomic DNA, cDNA, mRNA, tRNA, rRNA, hybrid sequences or synthetic or semi-synthetic sequences. These nucleic acids may be of human, animal, plant, bacterial, viral etc. origin. They may be obtained by any technique known to those skilled in the art, and in particular by the screening of banks, by chemical synthesis or by mixed methods including the chemical or enzymatic modifications of sequences obtained by the screening of banks. They may moreover be incorporated into vectors, such as plasmid vectors.

As regards more particularly the deoxyribonucleic acids they may be single- or double-stranded. These deoxyribonucleic acids may bear therapeutic genes, sequences for regulating transcription or replication, modified or unmodified antisense sequences, regions for binding to other cell components, etc.

In the sense of the invention, the term therapeutic gene is understood in particular to refer to any gene which codes for a protein product having a therapeutic effect. The protein product thus encoded may be a protein, a peptide, etc. This protein product may be homologous with respect to the target cell (that is to say a product which is normally expressed in the target cell when the latter exhibits no pathology). In this case, the expression of a protein makes it possible, for example, to overcome an insufficient expression in the cell or the expression of a protein which is inactive or weakly active on account of a modification, or alternatively of overexpressing the said protein. The therapeutic gene may thus code for a mutant of a cell protein, having increased stability, modified activity, etc. The protein product may also be heterologous with respect to the target cell. In this case, an expressed protein may, for example, make up or provide an activity which is deficient in the cell, enabling it to combat a pathology or to stimulate an immune response.

Among the therapeutic products, in the sense of the present invention, which may more particularly be mentioned are enzymes, blood derivatives, hormones, lymphokines, interleukins, interferons, TNF, etc. (FR 92/03120), growth factors, neurotransmitters or their precursors or synthetic enzymes, trophic factors: BDNF CNTF, NGF, IGF, GMF, aFGF, bFGF, NT3, NT5, HARP/pleotrophin, etc., dystrophin or a minidystrophin (FR 91/11947), the CFTR protein associated with mucoviscidosis, tumour-suppressant genes p53, Rb, Rap1A, DCC, k-rev, etc. (FR 93/04745), genes coding for factors involved in coagulation, factors VII, VIII, IX, genes involved in DNA repair, suicide genes (thymidine kinase, cytosine deaminase), haemoglobin genes or genes of other transport proteins, the genes corresponding to the proteins involved in the metabolism of lipids, of apolipoprotein type chosen from the A-I, A-II, A-IV, B, C-I, C-II, C-III, D, E, F, G, H, J and apo(a) apolipoproteins, metabolic enzymes such as, for example, lipoprotein lipase, hepatic lipase, lecithin cholesterol acyltransferase, 7-alpha-cholesterol hydroxylase and phosphatidic acid phosphatase, or lipid transfer proteins such as the cholesterol ester transfer protein and phospholipid transfer protein, an HDL-binding protein or a receptor chosen from, for example, LDL receptors, chylomicron-remnant receptors and scavenger receptors, etc.

The therapeutic nucleic acid may also be an antisense sequence or a gene whose expression in the target cell makes it possible to control the expression of genes or the transcription of cellular mRNA. Such sequences may, for example, be transcribed in the target cell into complementary RNA of cellular mRNA and thus block their translation into protein, according to the technique described in patent EP 140,308. The therapeutic genes also comprise the sequences coding for ribozymes which are capable of selectively destroying target RNA (EP 321,201).

As indicated above, the nucleic acid may also contain one or more genes coding for an antigenic peptide, capable of generating an immune response in humans or animals. In this particular embodiment, the invention thus makes it possible to produce either vaccines or immunotherapeutic treatments applied to humans or to animals, in particular against microorganisms, viruses or cancers. They may in particular be antigenic peptides specific for Epstein Barr virus, for HIV virus, for hepatitis B virus (EP 185,573), for pseudo-rabies virus, for syncitia-forming virus, for other viruses or alternatively specific for tumours (EP 259,212).

Preferably, the nucleic acid also comprises sequences which allow the expression of the therapeutic gene and/or of the gene coding for the antigenic peptide in the desired cell or organ. These may be sequences which are naturally responsible for expression of the gene considered when these sequences are capable of functioning in the infected cell. They may also be sequences of other origin (responsible for the expression of other proteins, or even synthetic). In particular, they may be promoter sequences for eukaryotic or viral genes. For example, they may be promoter sequences derived from the genome of the cell which it is desired to infect. Similarly, they may be promoter sequences derived from the genome of a virus. In this regard, there may for example be mentioned the promoters of genes E1A, MLP, CMV, RSV, etc. In addition, these expression sequences may be modified by addition of activation sequences, regulation sequences, etc. It may also be an inducible or repressible promoter.

Moreover, the nucleic acid may also contain, in particular upstream of the therapeutic gene, a signal sequence which directs the therapeutic product synthesized into the secretion pathways of the target cell. This signal sequence may be the natural signal sequence of the therapeutic product, but it may also be any other functional signal sequence, or an artificial signal sequence. The nucleic acid may also contain a signal sequence which directs the therapeutic product synthesized towards a particular compartment of the cell.

In another embodiment, the present invention relates to compositions comprising a nucleic acid, a lipopolyamine as claimed and an adjuvant capable of associating with the lipopolyamine/nucleic acid complex and of improving the transfecting power thereof. The Applicant has indeed shown that the transfecting power of lipopolyamines may, unexpectedly, be increased in the presence of certain adjuvants (lipids or proteins for example), capable of associating with the lipopolyamine/nucleic acid complex.

More preferably, the compositions of the invention comprise one or more neutral lipids as adjuvants. Such compositions are particularly advantageous, especially when the ratio R is low. The Applicant has indeed shown that the addition of a neutral lipid makes it possible to improve the formation of the nucleolipid particles and, surprisingly, to promote the penetration of the particle into the cell by destabilizing its membrane.

More preferably, the neutral lipids used in the context of the present invention are lipids containing 2 fatty chains.

In a particularly advantageous manner, natural or synthetic lipids, which may be zwitterionic or devoid of ionic charge under the physiological conditions, are used. They may be chosen more particularly from dioleoylphosphatidylethanolamine (DOPE), oleoylpalmitoylphosphatidylethanolamine (POPE), di-stearoyl, -palmitoyl, -myristoyl phosphatidylethanolamines as well as derivatives thereof N-methylated 1 to 3 times, phosphatidylglycerols, diacylglycerols, glycosyldiacylglycerols, cerebrosides (such as galactocerebrosides in particular), sphingolipids (such as sphingomyelins in particular) or alternatively asialogangliosides (such as asialoGM1 and GM2 in particular).

These various lipids may be obtained either by synthesis or by extraction from organs (example: brain) or from eggs, by standard techniques well known to those skilled in the art. In particular, the extraction of natural lipids may be performed using organic solvents (see also Lehninger, Biochemistry).

The compositions of the invention preferably comprise from 0.1 to 20 equivalents of adjuvant per one equivalent of compound of general formula I and, more preferably, from 1 to 5.

The compositions according to the invention may be formulated for the purpose of topical, cutaneous, oral, rectal, vaginal, parenteral, intranasal, intravenous, intramuscular, subcutaneous, intraoccular, transdermal, etc. administration. The pharmaceutical compositions of the invention preferably contain a vehicle which is pharmaceutically acceptable for an injectable formulation, in particular for direct injection into the desired organ, or for topical administration (to skin and/or mucous membrane). They may be in particular be sterile, isotonic solutions or dry compositions, in particular freeze-dried compositions, which, by addition depending on the case of sterilized water or of physiological saline, allow injectable solutions to be made up. The doses of nucleic acid used for the injection and the number of administrations may be adapted according to various parameters, and in particular according to the mode of administration used, the pathology concerned, the gene to be expressed, or alternatively the desired duration of the treatment. As regards more particularly the mode of administration, this may be either direct injection into the tissues or a treatment of cells in culture followed by their reimplantation in vivo, by injection or graft.

The present invention thus provides a particularly advantageous method for the treatment of diseases, comprising the in vivo or in vitro administration of a nucleic acid capable of correcting the said disease, in combination with a compound of general formula I under the conditions defined above. More particularly, this method may be applied to diseases resulting from a deficiency of a protein or nucleic acid product and the nucleic acid administered codes for the said protein product or contains the said nucleic acid product.

The invention covers any use of a lipopolyamine according to the invention for the in vivo or in vitro transfection of cells.

The present invention will be described more fully using the examples which follow, which should be considered as being non-limiting illustrations.

ABBREVIATIONS AND SYMBOLS

| | |
|---|---|
| EtOAc | Ethyl acetate |
| BOP | Benzotriazol-1-yloxytris(dimethylamino)phosphonium hexafluorophosphate |
| DCC | Dicyclohexylcarbodiimide |
| DCU | Dicyclohexylurea |
| DMAP | 4-Dimethylaminopyridine |
| DMF | Dimethylformamide |
| DMSO | Dimethyl sulphoxide |
| DODA | Dioctadecylamine |
| PE | Petroleum ether |
| EtOH | Ethanol |
| $Et_3N$ | Triethylamine |
| Rf | Coefficient of frontal retention |
| TFA | Trifluoroacetic acid |
| THF | Tetrahydrofuran |
| TMS | Tetramethylsilane |
| UV | Ultraviolet |

EQUIPMENT AND METHODS

A. Products Used

The DODA, the $Et_3N$, the TFA, the L-ornithine, the tetramethylammonium hydroxide, the Raney nickel and the diglycolic anhydride are from Fluka; the BOP is from Propeptide France; the DMAP, the isobutyl chloroformate and the N-methylmorpholine are from Aldrich. The ThF is from Merck; all the other solvents used are RP Prolabo products. The NaCl and $NaHCO_3$ solutions are saturated, the $KHSO_4$ solution is 0.5 M.

B. Physical Measurements

The proton nuclear magnetic resonance spectra ($^1H$ NMR) were recorded on a Bruker spectrometer.

The chemical shifts are expressed in ppm relative to TMS.

C. Chromatography on Silica

Thin layer chromatography (TLC) was carried out on Merck silica gel plates 0.2 mm in thickness.

Visualization:

by UV (254 nm)

with ninhydrin, by vaporizing (gentle spray) an ethanolic solution of ninhydrin (40 mg/100 ml EtOH) in order to visualize amines or amides, heating to 150° C.

with fluorescamine, by vaporizing a solution (40 mg/100 ml acetone) in order to visualize primary amines with iodine, by covering the plate with iodine powder Column chromatography was carried out on Merck 60 silica gel of particle size 0.063–0.200 mm

EXAMPLE 1

Synthesis of 2,5-bis(3-aminopropylamino)pentyl (dioctadecylcarbamoylmethoxy)acetate

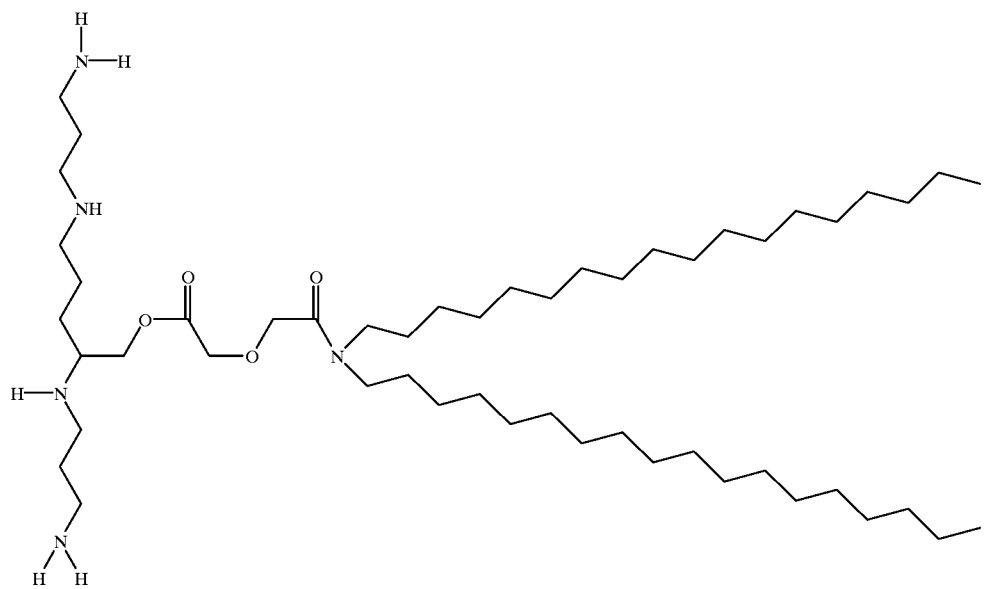

1.a Preparation of tetramethylammonium 2,5-bis(2-cyanoethylamino)pentanoate (1.a)

(S)-2,5-diaminopentanoic acid (L-ornithine) monohydrochloride (6.74 g, 40 mmol) and tetramethylammonium hydroxide pentahydrate (14.48 g, 80 mmol) are dissolved in methanol (20 ml). The water formed and the methanol are evaporated off under reduced pressure (using an oil pump) so as to obtain a dry residue.

N,N-Dimethylformamide (30 ml) is added to the salts obtained above. The mixture is degassed with nitrogen and then stirred vigorously for ten minutes, which allows the tetramethylammonium 2,5-diaminopentanoate to the solubilized (the tetramethylammonium chloride remains in suspension in the DMF).

Acrylonitrile (6 ml, 85.6 mol) is added dropwise; the flask warms up gently. The reaction mixture is left for 1 h at room temperature, under nitrogen. It is then filtered in order to remove the tetramethylammonium chloride. The DMF is evaporated off under reduced pressure. The residue obtained is an oily liquid; it solidifies when removed from the rotary evaporator. Acetonitrile (100 ml) is added and the flask is heated gently until a clear solution is obtained. THF is added until a cloudy solution is obtained. The flask is stored for two days in the freezer: the tetramethylammonium salt of L-2,5-bis(2-cyanoethylamino)pentanoic acid is recovered by filtration, in the form of a white solid. It is rinsed with THF on a sinter and then dried over $P_2O_5$. 6.06 g are obtained, equivalent to a yield of 49% (crude).

1.b Preparation of the tetramethylammonium salt of 2,5-bis (3-aminopropylamino)pentanoic acid (1.b)

Product 1.a is dissolved in a mixture of ethanol (18 ml), water (2 ml) and 2M potassium hydroxide (5 ml). The solution is flushed with argon. Raney nickel (2 ml of the Fluka suspension) is added. Hydrogenation is performed in an autoclave, flushed with nitrogen, at 26° C. In 3 h, the pressure goes from 50.6 bar to 44.7 bar, and then stabilizes for more than one hour. The autoclave has a capacity of 250 ml and the reaction mixture is 30 ml. The suspension obtained is filtered, rinsed with water and placed on a rotary evaporator. A yellow oil is obtained. The fluorescamine test is positive.

1.c Preparation of 2,5-bis{tert-butoxycarbonyl[3-(tert-butoxycarbonylamino)propyl]-amino}pentanoic acid (1.c)

Product 1.b is dissolved in dioxane (30 ml). Di-tert-butyl dicarbonate (17.46 g; 80 mmol) is added dropwise. The mixture is stirred overnight. The dioxane is evaporated off. $KHSO_4$ is added. The product is extracted with $CHCl_3$ (3×100 ml). The organic phase is then washed successively with $NaHCO_3$ (ph=7.5), NaCl and then dried over $MgSO_4$ and evaporated under reduced pressure. 10 g of product are obtained (15.4 mmol, equivalent to a yield of 39% relative to the ornithine).

HPLC: $MeCN/H_2O$: 0–3 min 50% MeCN, 3–20 min 50–100% MeCN, 20–40 min 100% MeCN, K'=7.96 (RP-18 column, flow rate=1 ml/min); TLC: $Rf(CHCl_3:EtOAc; 95:5 (v:v))=0.28$; NMR (ppm): 1.3 (m, 8H, $N+CH_2—CH_2—CH_2—CHN+COO/2\times N+CH_2CH_2CH_2N+$); 2.7–3.0 (m, 10H 5×N+$CH_2$); 3.8 (t, 1H, N+CHCOO); MS: $ME^+$=647, (MW=646).

1.d Preparation of 2,5-bis{tert-butoxycarbonyl[3-(tert-butoxycarbonylamino)propyl]amino}pentan-1-ol (1.d)

L-5-Carboxytetra-tert-butoxycarbonylspermine (1.94 g; 3 mmol) is dissolved in 30 ml of THF. 370 ml (3.1 mmol) of N-methylmorpholine are introduced using a micropipette. The reaction mixture, placed under nitrogen, is cooled to −15° C. (in a bath of cardice and ethylene glycol); 390 ml (3.1 mmol) of isobutyl chloroformate are then added. After three minutes, the reaction mixture is poured into a beaker containing $NaBH_4$ (2 g) dissolved in 20 ml of water at 4° C. The THF is evaporated off. $KHSO_4$ is added (to pH=7). The product is extracted with EtOAc, rinsed with $NaHCO_3$, NaCl, dried over $MgSO_4$, filtered and then evaporated. 1.15 g are obtained, equivalent to a yield of 61%.

TLC gives two spots; separation on a column of silica with the same eluant is thus performed and gives 0.97 g of product (yellow oil). The yield for the separation is 84%.

The yield for the reduction is 51%.

TLC: $Rf(PE:EtOAc: 1:1 (v\ v))=0.24$; NMR (ppm): 1.42 (s, 4×Boc); 1.5–1.7 (m, 8H $N+CH_2—CH_2—CH_2—CHN/2\times N+CH_2CH_2CH_2N$); 2.85–3.2 (m, 10H 5×$NCH_2$), 3.4 (m, 1H, $NCHCH_2OH$), 3.7 (d, 2H, $CH_2OH$), 6.8 (m, 2H; NH); MS: $MH^+$=633. MW=632.

1.e Preparation of 2,5-bis[3-(tert-butoxycarbonylamino) propyl-{tert-butoxycarbonylamino}pentyloxycarbonylmethoxyacetic acid (1.e)

0.51 g (0.806 mmol) of product 1.d are dissolved in 10 ml of $CH_2Cl_2$; 2 equivalents of diglycolic anhydride (1.535 mmol; 0.178 g), 2.2 equivalents of triethylamine (1.687 mmol; 235 µl) and 5 mg of DMAP are added. After one hour, with TLC showing that the alcohol has reacted, $CH_2Cl_2$ is added, and the mixture is then washed with 3×50 ml of $KHSO_4$, 3×50 ml of NaCl, dried over $MgSO_4$, filtered and then evaporated. 0.26 g of solid are obtained, equivalent to a yield of 43%.

TLC: $Rf(CHCl_3:MeOH:AcOH;\ 90:8:2\ (v:v:v))=0.75$; MS: $MH^+$=749, MW=748.

1.f Preparation of 2,5-bis{tert-butoxycarbonyl[3-(tert-butoxycarbonylamino)propyl]amino}pentyl dioctadecylcarbamoylmethoxy)acetate (1.f)

0.123 g of the above product (0.164 mmol), 1 equivalent (0.0856 g) of dioctadecylamine, 3 equivalents of triethylamine (68.4 ml) and 1.1 equivalent (0.0798 g) of BOP are dissolved in $CHCl_3$. The reaction mixture is stirred at room temperature. After two hours, 100 ml of $CH_2Cl_2$ are added and the mixture is then washed with 3×100 ml of $KHSO_4$, $NaHCO_3$, NaCl (to pH=7), dried and then evaporated. 0.13 g of product is obtained, equivalent to a yield of 63%.

TLC: Rf (PE:EtOAc: 1:1 (v:v))=0.62; visualization with iodine, ninhydrin and fluorescamine; NMR (ppm) 0.90 (t, J=7.5 Hz, 6H; $CH_3$, 1.20–1.75 (m, 108H: $CH_2/C(CH_3)_3$), 3.05–3.35 (m, 14H: $CH_2N$), 4.15–4.35 (m, 3H: $NCHCH_2OCO$), 4.23–4.27 (2s, 2×2H, $OCH_2CO$), 4.5–5.5 (broad m, 2H: NH); MS: $MH^+$=1252. MW=1251; Elemental analysis empirical formula: $C_{71}H_{137}N_5O_{12}$. % theory: C 68.06 H 11.02 N 5.59 % found: C 67.14 H 11.93 N 5.86.

1.g Preparation of 2,5-bis(3-aminopropylamino)pentyl (dioctadecylcarbamoylmethoxy)acetate (1.g)

1 ml of TFA is added to 0.025 g of product 1.f (0.02 mmol) in a 1.5 ml "Eppendorf"® tube and is left for one hour at room temperature. The TFA is evaporated off.

500 µl of ethanol are added so as to obtain a 40 mM solution, which is required for the biological tests.

MS: $MH^+$=852, MW=851.

EXAMPLE 2

Preparation of 1,3-bis(3-aminopropylamino)-2-propyl (dioctadecylcarbamoylmethoxy)acetate (2.f)

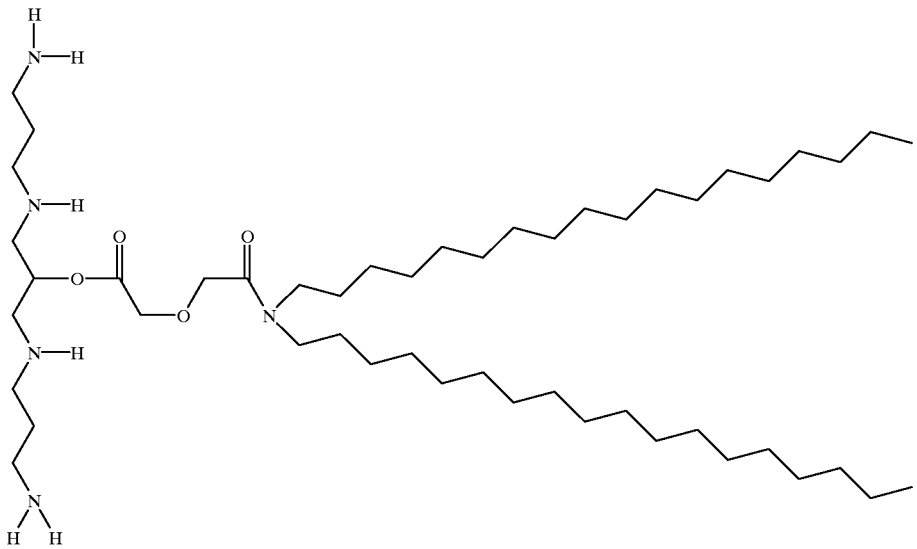

2.a Preparation of 1,3-bis(2-cyanoethylamino)propan-2-ol (2.a)

3.6 g (40 mmol) of 1,3-diaminopropan-2-ol are dissolved in 75 ml of methanol. 5.76 ml (80 mmol) of acrylonitrile are added over 15 minutes. The fluorescamine test is positive. The reaction mixture remains colourless. It is left stirring at room temperature overnight. The fluorescamine test is then negative. The methanol is evaporated off. 7.9 g of product are collected (100% yield for the crude product).

2.b Preparation of 1,3-bis(3-aminopropylamino)propan-2-ol (2.b)

Hydrogenation is performed in an autoclave, flushed with nitrogen, at 27° C.

Product 2.a is dissolved in a mixture of 15 ml of methanol, 10 ml of ethanol and 5 ml of KOH (2M). The solution is flushed with argon and 4 ml of the Raney nickel suspension are added to the autoclave.

In 3 h 30, the pressure goes from 51.6 bar to 37.6 bar then stabilizes for more than one hour. The autoclave has a capacity of 250 ml and the reaction mixture is 30 ml. The suspension obtained is filtered, rinsed with water and placed on a rotary evaporator. A yellow oil is obtained. The fluorescamine test is positive.

2.c Preparation of 1,3-bis{3-tert-butoxycarbonylamino(tert-butoxycarbonylaminopropyl)-2-propan-2-ol (2.c)

Product 2.b is protected in the same manner as in 1.c. 100 ml of $CH_2Cl_2$ are added. 39.2 g (179 mmol) of di-tert-butyl dicarbonate dissolved in 100 ml of dioxane are added dropwise. The solution is left stirring for 72 h. The solvent is evaporated off and $KHSO_4$ is added. The product is extracted with EtOAc (3×100 ml); the phases are combined and rinsed with $KHSO_4$, with $NaHCO_3$, with NaCl, dried over $MgSO_4$ and evaporated. 20 g are obtained (yield of 83% relative to the initial product).

The product crystallizes from PE.

TLC: Rf (PE:EtOAc: 1:1 (v:v))=0.23; Rf (PE:EtOAc: 1:2 (v:v))=0.63; NMR (ppm): 1.4 (2s, 36H: 4×($CH_3$)$_3$); 1.65 (qt, 4H; 2×$NCH_2CH_2CH_2NH$); 2.95 (q, 4H; 2×$NHCH_2CH_2$); 3.1 (2d, 4H; $NCH_2CHCH_2$); 3.2 (t, 4H; $NCH_2CH_2$); 3.85 (m, 1H; OH); 5.9 (s, 2H; NH); MS: $MH^+$=605, MW=604.

2.d Preparation of 1,3-bis{3-tert-butoxycarbonylamino(tert-butoxycarbonylaminopropyl}-2-propyl-2-ethoxycarbonylmethoxyacetic acid (2.d)

604 mg (1 mmol) of product 2.c are dissolved in 20 ml of $CH_2Cl_2$. 2 equivalents of anhydride (2 mmol; 0.232 g), 2.2 equivalents of $Et_3N$ (307 µl and then 100 µl) and 6.5 g of DMAP are introduced. After stirring for 24 hours at room temperature, $CH_2Cl_2$ is added and the mixture is washed with $KHSO_4$, with NaCl, dried over $MgSO_4$, filtered and then evaporated. 0.156 g of product is obtained (22% yield).

TLC: Rf($CHCl_3$:MeOH:AcOH: 90:8:2 (v:v:v))=0.71; NMR (ppm): 1.2–1.4 (2s, 36H 4×($CH_3$)$_3$): 1.5 (m, 4H: 2×$NHCH_2CH_2CH_2N$), 2.85 (q, 4H, 2×$NHCH_2CH_2$); 3.1 (m, 8H; 4×$NCH_2$); 3.9–4.2 (2s, 4H; 2×$OCH_2COO$); 5.25 (m, 1H: $CH_2CHCH_2$); 6.7 (2H; NH); MS: $MH^+$=721, MW=720.

2.e Preparation of 1,3-bis{3-tert-butoxycarbonylamino(tert-butoxycarbonylaminopropyl}-2-propyl (dioctadecylcarbamoylmethoxy)acetate (2.e)

0.216 mmol of acid 2.d are dissolved in 3 ml of $CHCl_3$. 1 equivalent of DODA (0.113 g), 3 equivalents of $Et_3N$ (100 µl) and 1.1 equivalents of BOP (0.11 g) are added. The reaction mixture is stirred at room temperature for 24 h. The $CHCl_3$ is evaporated off. 100 ml of EtOAc are added. The organic phase is washed with HCl (0.5 M), with $NaHCO_3$, with NaCl to pH=7, dried over $MgSO_4$ and then evaporated. 0.185 g is obtained (70% yield). A column is performed on silica. 110 mg of product are collected (42% yield).

TLC: Rf($CHCl_3$:MeOH:ACOH: 90:8:2 (v:v:v))=0.81; Rf(PE; EtOAc: 1:1 (v:v))=0.67; NMR (ppm) 0.85 (t, 6H; 2×$CH_3$); 1.20–1.55 (m, 100H; $CH_2$/C($CH_3$)$_3$), 1.6 (m, 4H; 2×$NHCH_2CH_2CH_2N$); 3.05–3.4 (m, 16H; 2×$NHCH_2CH_2CH_2N/NCH_2CHCH_2N/2×CH_2N$); 4.1 (s, 2H; $NCOCH_2O$); 4.15 (s, 2H; $OCH_2COO$); 5.25 (m, 1H; $CH_2CHCH_2$), 6.15 (m, 2H; NH); MS: $MH^+$=1224, MW=1223.

2.f Preparation of 1.3-bis{3-tert-butoxycarbonylamino(tert-butoxycarbonylaminopropyl}-2-propyl (dioctadecylcarbamoylmethoxy)acetate (2.f)

1 ml of TFA is added to 0.0247 g of product 2.e (0.021 mmol) in a 1.5 ml "Eppendorf"® tube and the mixture is left for one hour at room temperature. The TFA is evaporated off.

505 μl of ethanol are added so as to obtain a 40 mM solution, which is required for the biological tests.
MS: MH$^+$=824, MW=823;

EXAMPLE 3

Preparation of 2-(3-aminopropylamino)-1-(3-aminopropylaminomethyl)ethyl (N,N-dioctadecyl) succinamate

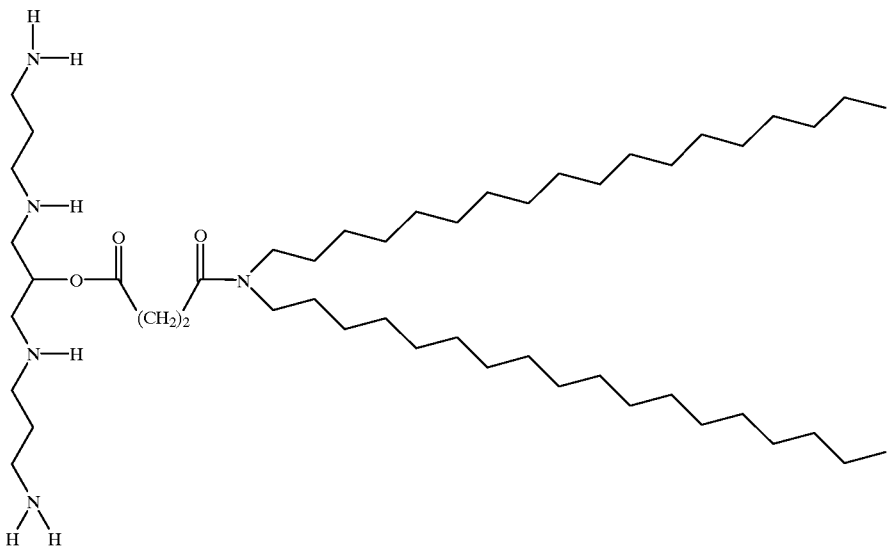

This compound is prepared according to the procedure described above in Example 2, replacing the diglycolic acid by succinic acid.

Mass spectrometric analysis of the product thus obtained indicates an MH$^+$ fragment of 808, which is in accordance with the expected mass.

USE OF LIPOPOLYAMINES ACCORDING TO THE INVENTION FOR THE IN VITRO TRANSFECTION OF GENETIC MATERIAL

A. Plasmids used for the in vitro Gene Transfer

Plasmid pCMV-LUC is used. This is a construction containing the "luciferase" reporter gene, derived either from the plasmid pGL2-basic vector (Promega) or from the plasmid pGL2-control vector (Promega) by insertion of a fragment Mlu I-Hind III containing the promoter of human cytomegalovirus (CMV), extracted from the vector plasmid pcDNA3 (Invitrogen).

B. Procedure for the Preparation of the Solutions used for the Transfection

Lipopolyamines prepared according to the above examples are dissolved to a concentration of 40 mM in ethanol and then diluted in an ethanol/water mixture, maintaining an ethanolic concentration of less than 10%.

The solutions of nucleic acid to be transfected are diluted with physiological saline (0.15M NaCl) and then added to the lipopolyamine solutions, in a 1/1 ratio (v/v). After vortex homogenization and incubation for 15 minutes at room temperature, the DNA/lipopolyamine solutions are distributed at a final concentration of 9% (v/v) in wells, in which the cells were washed with protein-free culture medium (serum).

EXAMPLE 4

Influence of the Charge Ratio (amine/phosphate) on the Efficiency of Transfection Samples of 1×10$^5$ NIH 3T3 cells in exponential growth phase on 2 cm$^2$ are treated with lipopolyamine/pCMV-LUC solutions having variable charge ratios, for 4 hours at 37° C. under 5% $CO_2$; each sample receives 1 μg of nucleic acid. Search for the expression of the reporter gene is carried out after addition of foetal calf serum to a final concentration of 8%, followed by incubation for 40 hours in a $CO_2$ oven.

The luciferase activity is assayed by light emission [RLU=relative light unit] in the presence of luciferin, coenzyme A and ATP for 20 seconds and is expressed with reference to one μg of protein in the supernatant obtained after cell lysis. The results obtained are reported in Table 1 below.

TABLE 1

| | Lipopolyamine of Example 1 | | Lipopolyamine of Example 2 | |
|---|---|---|---|---|
| Charge ratio | Lumin-escence | Coeff. of var. (%) | Lumin-escence | Coeff. of var. (%) |
| 1 | 69 | 5 | 23 | 34 |
| 2 | 5091 | 3 | 252 | 6 |
| 4 | 3636 | 30 | 7890 | 3 |
| 6 | 21334 | 3 | 61401 | 5 |
| 8 | 40846 | 3 | 73224 | 2 |
| 10 | 55321 | 1 | 77633 | 2 |
| 12 | 53239 | 5 | 48634 | 5 |
| 14 | 36 | 10 | 52417 | 2 |
| DNA only | 52 | 5 | | |

Each value corresponds to the average of three independent tests.

This experiment shows clearly that the lipopolyamines according to the invention allow the transfer of genes under conditions required for their expression.

EXAMPLE 5

Influence of the Concentration of Nucleic Acid in DNA/Lipopolyamine Mixtures

According to the same procedure as that described in the above example, the NIH 3T3 cells are treated with DNA/lipopolyamine mixtures under conditions in which various concentrations of DNA are used for the same charge ratio. In this case, the luciferase activity is measured for 20 seconds and carried to $2.5 \times 10^3$ treated cells. The results are presented in Tables II and III below. Lipopolyamine of Example 1

TABLE II

| | Charge ratio | | | |
|---|---|---|---|---|
| μg DNA | x4 | x6 | x8 | x10 |
| 0.25 | 27(19) | 25(20) | 32(31) | 36(15) |
| 0.5 | 23(5) | 37(54) | 4476(4) | 4811(19) |
| 1.0 | 4945(12) | 19194(14) | 30933(21) | 39357(3) |
| 2.0 | 93937(2) | 105533(1) | 111167(14) | 8315(15) |
| 3.0 | 106293(11) | 100093(8) | 53475(12) | |
| 4.0 | 98553(10) | 69863(8) | | |

Lipopolyamine of Example 2

TABLE III

| | Charge ratio | | | |
|---|---|---|---|---|
| μg DNA | x4 | x6 | x8 | x10 |
| 0.25 | 40(17) | 52(64) | 122(14) | 51(5) |
| 0.5 | 28(10) | 204(25) | 36533(7) | 44473(7) |
| 1.0 | 3427(12) | 48167(13) | 49363(13) | 50083(9) |
| 2.0 | 33377(13) | 44697(18) | 30670(16) | 9544(4) |
| 3.0 | 9686(3) | 31557(2) | 9157(8) | |
| 4.0 | 4321(9) | 40105(10) | | |

Each value corresponds to the average of three independent tests.

The values given in parentheses correspond to the coefficient of variation, expressed as a %.

What is claimed is:

1. A lipopolyamine in D, L or DL form or a salt thereof, of formula I:

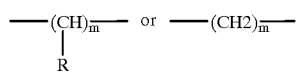

in which m is an integer from 2 to 6, n is an integer from 1 to 9 with a single group R other than hydrogen present in formula I and values of m which are different or identical in the various groups

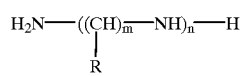

R represents hydrogen or a radical of formula II:

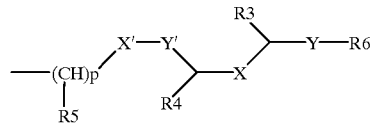

in which

X and X' independently represent oxygen, a methylene group —$(CH_2)_q$— with q equal to 0,1,2 or 3, or an amino group —NH— or —NR'— with R' representing a $C_1$ to $C_4$ alkyl group, Y and Y' independently represent a methylene group, a carbonyl group or a C=S group, $R_3$, $R_4$ and $R_5$ independently represent hydrogen or a substituted or unsubstituted $C_1$–$C_4$ alkyl radical, and p is an integer from 0 to 5, and $R_6$ represents a cholesterol derivative or an alkylamino group —$NR_1R_2$ with $R_1$ and $R_2$ independently representing a linear or branched, saturated or unsaturated $C_{12}$ to $C_{22}$ aliphatic radical.

2. A lipopolyamine according to claim 1, wherein n is an integer between about 1 and about 5.

3. A pharmaceutical composition, comprising a lipopolyamine according to claim 1 and a nucleic acid.

4. A composition according to claim 3, where the nucleic acid is a deoxyribonucleic acid.

5. A composition according to claim 3, where the nucleic acid is a ribonucleic acid.

6. A composition according to claim 3, where the nucleic acid is an antisense nucleic acid.

7. A composition according to claim 3, where the nucleic acid contains a therapeutic gene.

8. A composition according to claim 7, where said therapeutic gene codes for a protein involved in the metabolism of lipids, an enzyme, a lipid transfer protein, an HDL-binding protein or a receptor.

9. A composition according to claim 3, further comprising a vehicle which is a pharmaceutically acceptable injectable formulation.

10. A composition according to claim 3, further comprising a vehicle which is pharmaceutically acceptable for application to the skin or the mucous membranes.

11. A composition according to claim 8, wherein the therapeutic gene codes for (1) an apolipoprotein selected from the group consisting of A-I, A-II, A-IV, B, C-I, C-II, C-III, D, E, F, G, H, J and apo(a) apolipoproteins; (2) an enzyme selected from the group consisting of lipases, lecithin cholesterol acyltransferase, 7-alpha-cholesterol hydroxylase, and phosphatidic acid phosphatase; (3) a lipid transfer protein selected from the group consisting of cholesterol ester transfer protein and phospholipid transfer protein; or (4) a receptor selected from the group consisting of LDL receptors, chylomicron-remnant receptors and scavenger receptors.

12. A pharmaceutical composition comprising a lipopolyamine according to claim 1, a nucleic acid, and an adjuvant; wherein said lipopolyamine and said nucleic acid form a complex which associates with said adjuvant such that the transfecting power of the complex is improved relative to the absence of said adjuvant.

13. A composition according to claim 12, where the adjuvant is one or more neutral lipids.

14. A composition according to claim 13, where said neutral lipid or lipids are chosen from synthetic or natural lipids, which are zwitterionic or devoid of ionic charge under physiological conditions.

15. A composition according to claim 14, where said neutral lipid or lipids are lipids containing 2 fatty chains.

16. A composition according to claim 15, where said neutral lipid or lipids are chosen from dioleoylphosphatidylethanolamine (DOPE), oleoylpalmitoylphosphatidylethanolamine (POPE), di-stearoyl, -palmitoyl, -myristoyl phosphatidylethanolamines as well as derivatives thereof N-methylated 1 to 3 times; phosphatidylglycerols, diacylglycerols, glycosyldiacylglycerols, cerebrosides, sphingolipids and asialogangliosides.

17. A composition according to claim 12, which comprises from about 0.1 to about 20 equivalents of adjuvant per 1 equivalent of lipopolyamine.

18. A composition according to claim 16 wherein the lipid is galactocerebroside, sphingomyelin, asialoganglioside asialoGM1 or asialoganglioside GM2.

19. A composition according to claim 17, having from about 1 to about 5 equivalents of adjuvant per 1 equivalent of lipopolyamine.

20. A method of in vivo or in vitro transfection of cells comprising the step of administering to a cell the lipopolyamine according to claim 1.

21. A lipopolyamine in D, L or DL form or a salt thereof, of formula I:

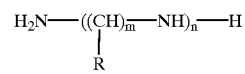

in which m is an integer from 2 to 6, n is an integer from 1 to 9 with a single group R other than hydrogen present in formula I and values of m which are different or identical in the various groups

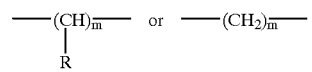

R represents hydrogen or a radical of formula II':

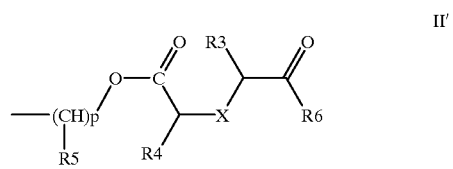

in which

X represents oxygen or a group —$(CH_2)_q$— with q equal to zero; $R_3$, $R_4$ and $R_5$ independently represent hydrogen or a substituted or unsubstituted $C_1$–$C_4$ alkyl radical, and p is an integer from 0 to 5, and $R_6$ represents a cholesterol derivative or an alkylamino group —$NR_1R_2$ with $R_1$ and $R_2$ independently representing a linear or branched, saturated or unsaturated $C_{12}$ to $C_{22}$ aliphatic radical.

22. The lipopolyamine of claim 21, of the formula III:

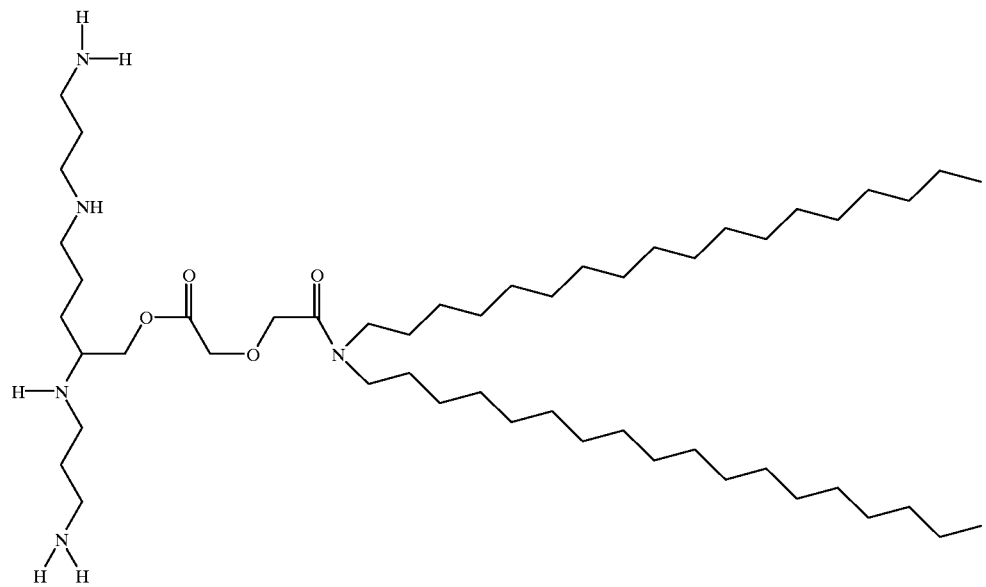

in D, L, or DL form or a salt thereof.
23. The lipopolyamine of claim 21, of the formula IV:
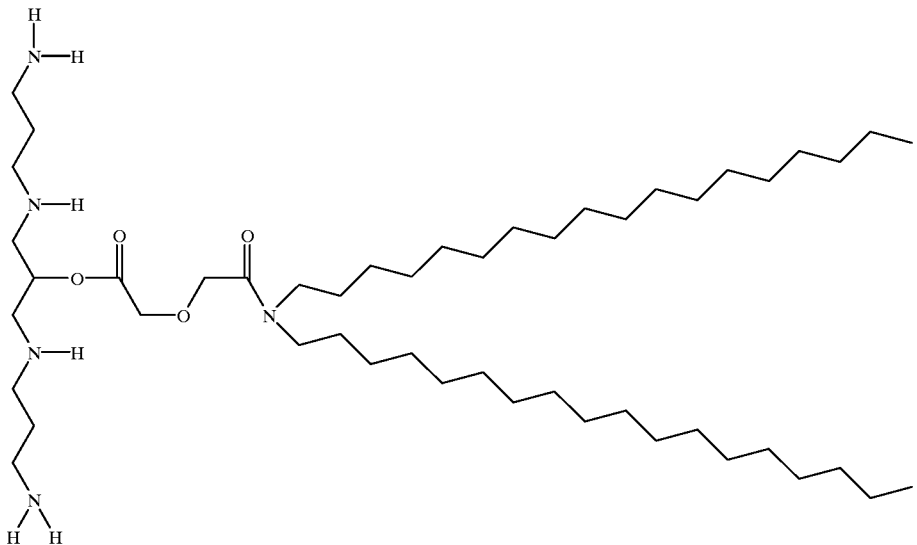
in D, L or DL form or a salt thereof.
24. A lipopolyamine of the formula V:
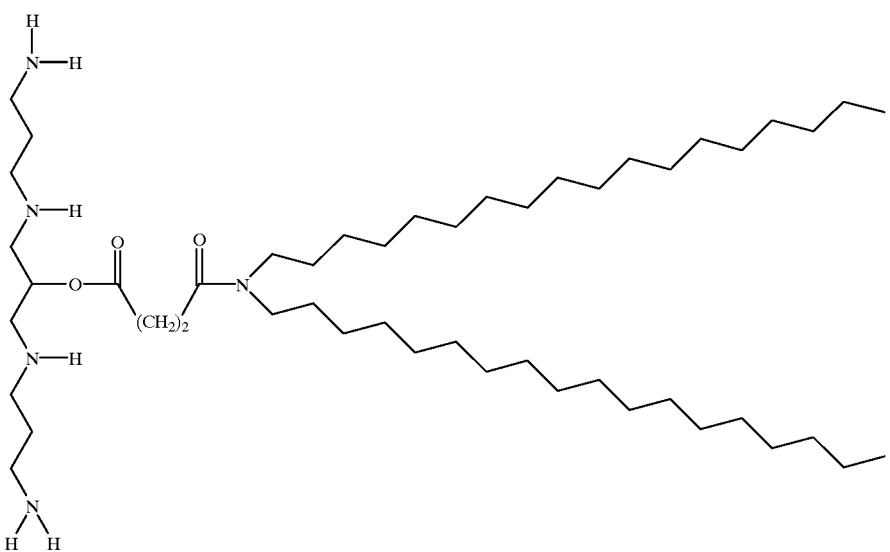
in D, L, or DL form or a salt thereof.

25. A lipopolyamine of the formula VI:
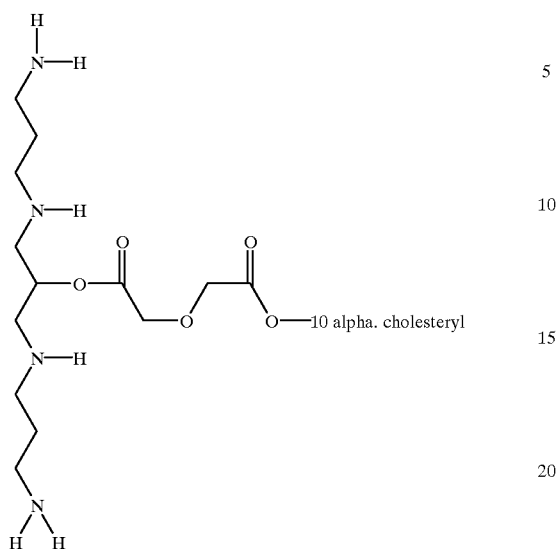
in D, L or DL form or a salt thereof.